United States Patent [19]

Fukada et al.

[11] Patent Number: 5,067,488
[45] Date of Patent: Nov. 26, 1991

[54] MASTICATION DETECTOR AND MEASUREMENT APPARATUS AND METHOD OF MEASURING MASTICATION

[75] Inventors: Eiichi Fukada, Kawasaki; Shigeru Saito, Zushi; Toshiharu Yagi, Toyonaka; Yoshihide Higashihata, Settsu, all of Japan

[73] Assignees: Daikin Industries, Ltd., Osaka; Shigeru Saito, Kanagawa, both of Japan

[21] Appl. No.: 613,444

[22] Filed: Nov. 13, 1990

Related U.S. Application Data

[63] Continuation of Ser. No. 341,953, Apr. 24, 1989, abandoned.

[30] Foreign Application Priority Data

Apr. 22, 1988 [JP] Japan .............................. 63-100885

[51] Int. Cl.[5] .............................................. A61B 5/103
[52] U.S. Cl. ............................................ 3305; 128/782
[58] Field of Search ................. 128/773, 774, 777, 782

[56] References Cited

U.S. PATENT DOCUMENTS

| | | | |
|---|---|---|---|
| 2,674,808 | 4/1954 | Tainter | 33/513 |
| 3,996,666 | 12/1976 | Blanque | 128/777 |
| 4,355,645 | 10/1982 | Mitani et al. | 128/777 |
| 4,444,200 | 4/1984 | Fujisaki et al. | 128/706 |
| 4,503,705 | 3/1985 | Polchaninoff | 73/172 |
| 4,559,953 | 12/1985 | Wright et al. | 128/773 |
| 4,592,727 | 6/1986 | Bloomfield | 433/71 |
| 4,669,477 | 6/1987 | Ober | 128/421 |
| 4,672,976 | 6/1987 | Kroll | 128/773 |
| 4,836,218 | 6/1989 | Gay et al. | 128/773 |

*Primary Examiner*—William E. Kamm
*Assistant Examiner*—Kevin Pontius
*Attorney, Agent, or Firm*—Wenderoth, Lind & Ponack

[57] ABSTRACT

A mastication measurement apparatus is provided with a displacement detecting element such as a piezoelectric element and a holder which keeps the detecting element in close contact with a part of the side of one's face. The apparatus is capable of processing electric signals produced by the detecting element to measure the number of masticating cycles, number of masticating cycles per unit time, a maximum value of the mastication force and the mastication energy, and is also capable of checking whether a denture is matched to a subject by detecting noises included in the output of the detecting element. In accordance with the invention, it is also possible to determine which teeth are not used during the mastication of food by attaching the detecting elements to both sides of a face and comparing the outputs from both detecting elements.

36 Claims, 4 Drawing Sheets

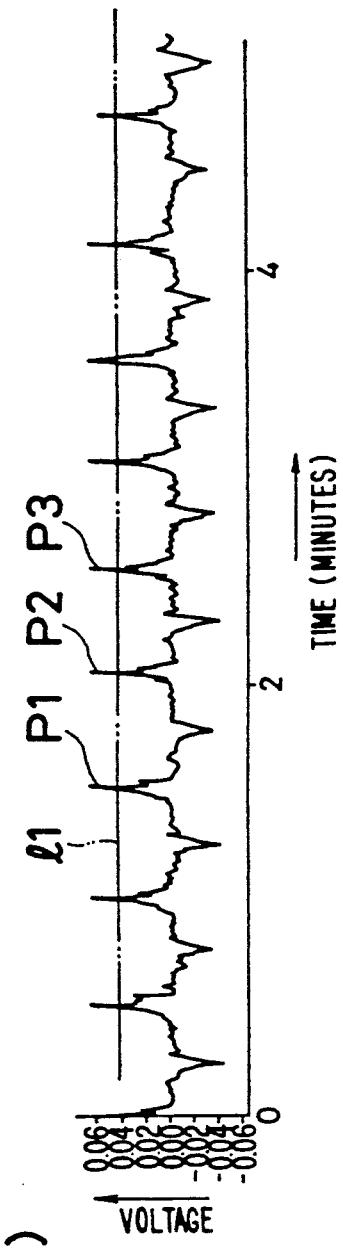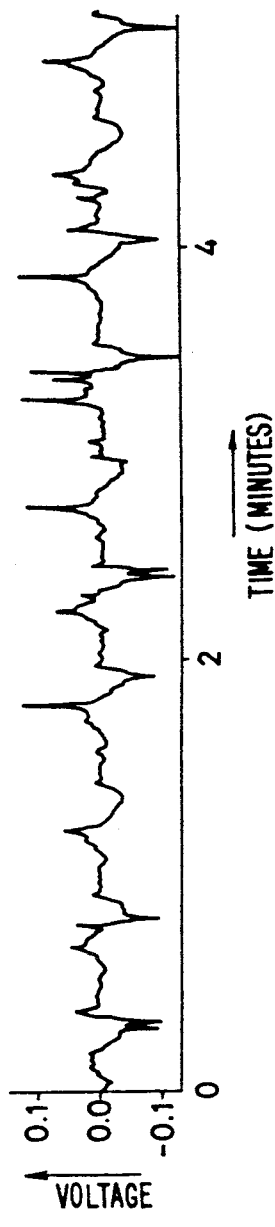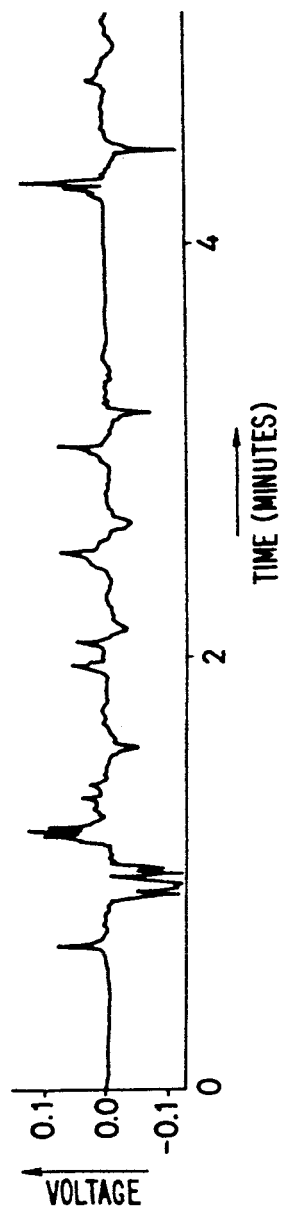

MASTICATION DETECTOR AND MEASUREMENT APPARATUS AND METHOD OF MEASURING MASTICATION

This application is a continuation of now abandoned application, Ser. No. 07/341,953 filed on Apr. 24, 1989.

BACKGROUND OF THE INVENTION

1. Field of the Invention

This invention relates to an apparatus for measuring mastication of humans and animals and a method thereof.

2. Description of the Prior Art

With the rapid changes in eating habits toward tender foods to a considerable extent, mastication of sufficient chewing and digestion characteristics is declining. Seventy-five percent of children of lower grades of elementary school, in particular, do not or cannot chew their food enough, according to a study. Such insufficient mastication results not only in physical disorders such as dysgnathia, teeth malalignment, dental caries and pyorrhea alveolaris, but also in mental disturbances such as hypomnesia.

For this reason, improvements in eating habits and the related environment are desired to encourage the public to masticate food sufficiently.

On the other hand, because a transition of emphasis in medical practice from therapeutic medicine to preventive and control medicine is expected in the future, dentists will give their patients post-therapeutic instructions to control and prevent the recurrence of dental problems, instead of mere therapeutic treatment. In this trend, research of mastication has become increasingly important.

In the prior art of measuring masticating cycles, a picture of a subject is recorded with a video camera, and the mastication cycles and the characteristics thereof are measured by playing back the recorded picture. Although this prior art process is practical, it requires a video camera and related equipment and constitutes an elaborate procedure. The prior art also has a drawback in that the measurement cannot be made when the subject turns sideways instead of facing toward the camera.

Another prior art process is the electromyograph method which includes a procedure similar to that of conventional electrocardiography, with sensors adhered to the face of the subject detecting the electric current generated thereat. These prior art processes are unable to measure the mastication easily.

SUMMARY OF THE INVENTION

The object of the invention is to provide an apparatus and a method for measuring mastication simply and accurately.

To achieve the above object, an apparatus for detecting mastication is provided comprising:

an element for detecting a displacement of a part of the side of a face, and holding means for maintaining the displacement detecting element in close contact with the part of the side of the face.

In a preferred embodiment of the invention, the displacement detecting element is a piezoelectric element.

Further, the part of the side of the face is preferably part of the masseter.

The holding means comprises a holding member which is U-shaped with both ends positioned at respective sides of the face, and fitting means for holding the displacement detecting element so as to face the part of the side of the face, and which fitting means is fitted to at least one end of the holding member.

In another preferred embodiment, the holding means is an adhesive tape for attaching the displacement detecting element to the side of the face.

Still further, the piezoelectric element is a bimorph element.

To further achieve the above object, an apparatus for measuring mastication is provided comprising:

an element for detecting a displacement of a part of the side of a face, holding means for maintaining the displacement detecting element in close contact with the part of the side of the face, and means for processing operable in response to the output of the displacement detecting element.

In the preferred embodiment, the displacement detecting element is a piezoelectric element.

In the preferred embodiment, the processing means counts a number of masticating cycles.

Also, the processing means may count the number of masticating cycles per unit time.

Further, the processing means can measure a mastication force corresponding to a peak value of the output of the displacement detecting element.

Still further, the processing means integrates the output of the displacement detecting element and measures mastication energy corresponding to the integrated value.

Still further, the processing means can detect noises included in the output of the displacement detecting element.

In a preferred embodiment, the processing means is capable of changing the threshold at which the output of the displacement detecting element is detected and counts the number of masticating cycles corresponding to the detected outputs.

To also achieve the above object, a method for measuring mastication is provided comprising steps of:

attaching a displacement detecting element to part of the side of a face, and displaying an output of the displacement detecting element with display means.

In accordance with the invention, because the displacement detecting element, for example a piezoelectric sensor, strain gage or the like, is held in close contact with the part of the side of a face by the holding means, mastication of a human or an animal can be measured in a natural condition, and the measurement is accurate and is conducted in a simple manner.

Also, the output of the displacement detecting element is processed by the processing means, so that the number of mastication cycles, the number of mastication cycles per unit time, the mastication force and the mastication energy can be measured. Moreover, the noises included in the output of the displacement detecting element can be discriminated to check, if the subject has a false tooth or false teeth, whether such false tooth or teeth are fitted well.

As is evident from the preceding description, because the invention enables the mastication to be measured by the displacement detecting element such as a piezoelectric element, the mastication measurement can be performed simply and accurately, and therefore no particular trouble is required of the subject other than masticating naturally, and the measurement apparatus is comfortable.

BRIEF DESCRIPTION OF THE DRAWINGS

Other objects, features and advantages of the invention will be better understood when the following detailed description is reviewed in conjunction with the drawings.

FIGS. 4(1), 4(2) and 4(3) are graphs of the waveforms of outputs from the displacement detecting element 3 of the apparatus shown in FIG. 1.

DETAILED DESCRIPTION OF THE PREFERRED EMBODIMENTS

Figure 1:
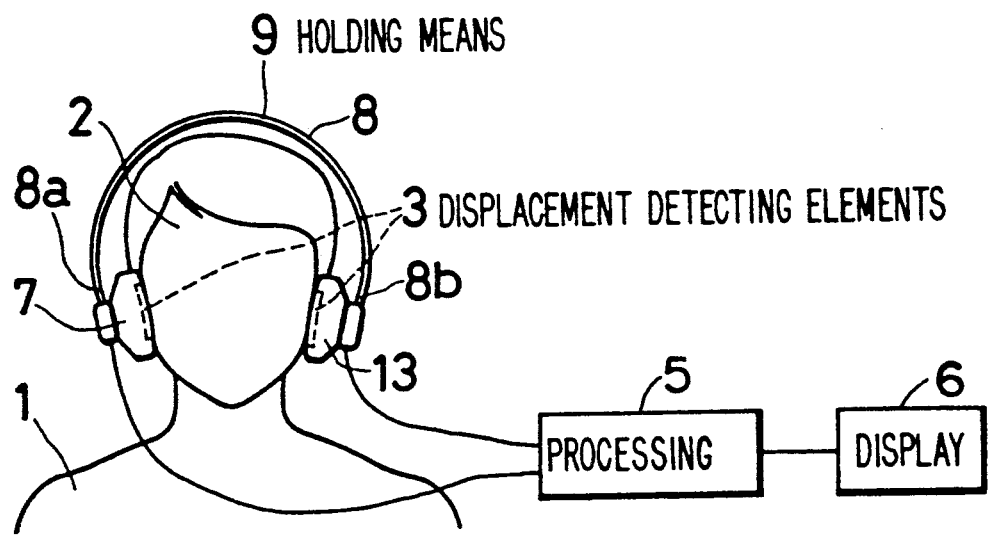
FIG. 1 is a schematic diagram of an embodiment of a masticating measuring apparatus according to the invention.

A preferred embodiment of the invention is explained below referring to the drawings.

Figure 2:
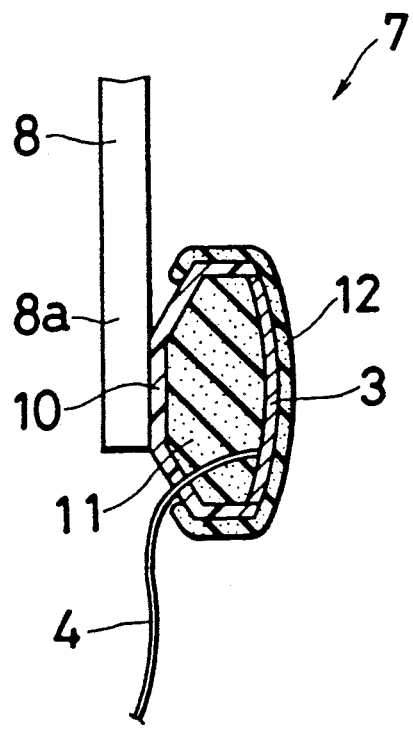
FIG. 2 is a cross-sectional view of a part of the apparatus shown in FIG. 1.

FIG. 1 shows an embodiment of the apparatus according to the invention and FIG. 2 is a cross-sectional view thereof. A displacement detecting element 3 is secured against the side of a face 2 of a subject 1 whose mastication is to be measured. The output from the displacement detecting element 3 is fed via a lead wire 4 to signal processing means 5 which incorporates a microcomputer and other equipment. The result of the measurement obtained by the processing means 5 is displayed by display means 6.

The side of the face 2 refers to a part of the face which is displaced during mastication, or more specifically, a part on the masseter or temporal muscle. Because the part of the face which undergoes displacements of the largest magnitude during mastication is the masseter, this part is preferably used. Particularly because the displacement is to be detected only during mastication, and displacements of parts of the face and cheek during conversation, for example, are not detected when the displacement detecting element is pressed against the masseter, this part is most suitable for use in the measurement of the number of mastication cycles and mastication force.

The displacement detecting element 3 is fitted to a holding member 8 by fitting means 7. The holding member 8 and the fitting means 7 constitute holding means 9. The holding member 8 is an elastic U-shaped band made of a metal, for example. One end 8a of the holding member 8 is fitted with the fitting means 7. The fitting means 7 is provided with a housing 10 and an elastic body 11 occupying the housing 10. The displacement detecting element 3 is held on the elastic body 11. The elastic body 11 is made of a material such as foamed synthetic resin or rubber. The displacement detecting element 3 is plate-like and has a convex shape as viewed from the side of the face 2, and is elastically pressed toward the face 2 by the elastic body 11. A peripheral surface of the displacement detecting element 3 and a part of the housing 10 are covered with a cover 12. The cover 12, made of a thin sponge or cloth, makes the contact of the fitting means 7 with the side of the face 2 comfortable and transmits the displacement of the part of the side of the face 2 to the displacement detecting element 3 certainly.

Figure 3:
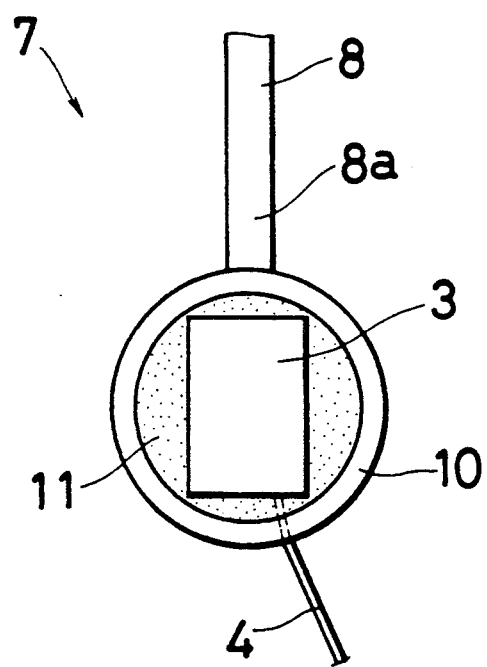
FIG. 3 is a front view of the holding means 7 with a cover 12 removed of the apparatus shown in FIG. 1.

FIG. 3 is a front view of the fitting means 7 shown in FIG. 2 with the cover 12 removed. The front face of the displacement detecting element 3 has, for example, a rectangular shape.

The displacement detecting element 3 may be a pressure sensitive element such as a piezoelectric element or a strain gage, or any other element which detects the displacement of part of the side of the face 2, and generates an electric signal of a level corresponding to the displacement of the part of the side of the face 2 during mastication. The piezoelectric element may comprise (a) high-molecular weight polymer of piezoelectric material, (b) ceramic piezoelectric material or (c) a compound of a high-molecular weight polymer and a ceramic piezoelectric material. The high-molecular weight polymer of piezoelectric material may be a natural high-molecular weight polymer of piezoelectric material or a synthetic high-molecular weight polymer of piezoelectric material, where the synthetic high-molecular weight polymer of piezoelectric material may be polyvinylidene fluoride, a vinylidene fluoride copolymer or a copolymer of vinylidene cyanide or vinyl acetate. The ceramic piezoelectric material may be barium titanium ($BaTiO_3$) or lead zirconate titanate (PZT). The compound is obtained by mixing the above-mentioned ceramic material into the above-mentioned high-molecular weight polymer. Among these, in view of flexibility, resistance to breakage and conformability to the displacement of a part of the face during mastication the piezoelectric element using high-molecular weight polymer of (a) or (c) above is preferred for the invention.

The piezoelectric element may be a so-called single structure, bimorph structure or multiple-layer structure, but in order to detect the change in the curvature of the part of the face due to the projection of the masseter during mastication such as described previously, a piezoelectric element of a bimorph structure is preferred.

While the displacement detecting element 3 is attached to at least one end 8a of the holding member 8, usually a similar detecting element 3 is attached to another end 8b by a fitting means 13.

FIGS. 4(1), 4(2) and 4(3) are graphs showing waveforms of the output from a displacement detecting element 3 in the form of a piezoelectric element. FIG. 4(1) shows a waveform obtained when the subject 1 repeats chewing movements without holding anything in the subject's mouth, FIG. 4(2) shows a waveform obtained when a male subject chews gum and FIG. 4(3) shows a waveform obtained when a female subject chews gum. As shown in FIG. 4(1), for example, the number of masticating cycles of the subject 1 is counted by the processing means 5 by discriminating the pulses obtained from the displacement detecting element 3 with reference to a predetermined threshold 11 and counting the pulses p1, p2, p3 which have levels higher than the threshold 11.

By counting the number of pulses p1, p2, p3 per unit time, i.e. the number of masticating cycles per unit time, a mastication speed can be obtained.

The peak value of the output pulses p1, p2, p3 of the displacement detecting element 3 corresponds to the mastication force. Therefore, a difference in the strength of the mastication of different kinds of food, tender or hard, can be measured.

The processing means 5 counts the pulses p1, p2, p3 which have levels higher than the threshold 11, and therefore counts only the mastication cycles of mastication forces greater than that corresponding to the threshold 11, thereby generating data from which instructions can be given to the subject 1, such as a child, to improve mastication.

Also, the processing means is capable of changing the threshold 11 above which the pulses are counted.

The processing means can also integrate the pulses p1, p2, p3 and thus measure mastication energy, thereby making it possible to analyze the mastication energy used when eating various foods.

Further the processing means 5 is capable of detecting noises included in the pulses p1, p2, p3 so that when a denture is applied to the subject 1, it may be checked as to whether the denture is matched to the subject 1. When the denture is not matched to the subject 1, a large amount of noise is detected when the subject 1 chews gum or the like. Thus, while the matching of dentures has conventionally been checked by dentists conducting tests over a long time, for example 2 or 3 days, according to the invention the matching of dentures can be tested in a very short time with the denture fitted to the subject 1.

Further, the use of a side of the face which includes an impairment of the teeth on that side, a weak side as it were, is generally avoided during mastication. Therefore this invention can be applied to detect the weak side earlier. For such diagnosis, output waveforms of the displacement detecting elements 3 secured to the sides of the face by the right and left fitting means 7 and 13 are compared. The output waveform obtained from one of the two displacement detecting elements secured to the side having weak teeth which is not used during mastication has lower amplitudes. Therefore it can be determined that the teeth on the side of the displacement detecting element 3 which outputs lower amplitude waves are the weaker teeth.

Figure 5:
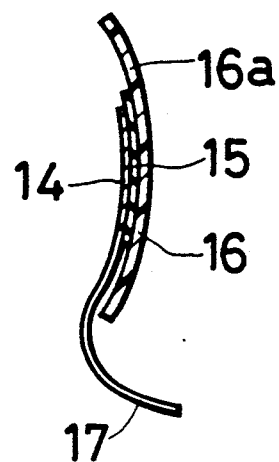
FIG. 5 is a cross-sectional view of a part of another embodiment of a masticating measuring apparatus according to the invention.
Figure 6:
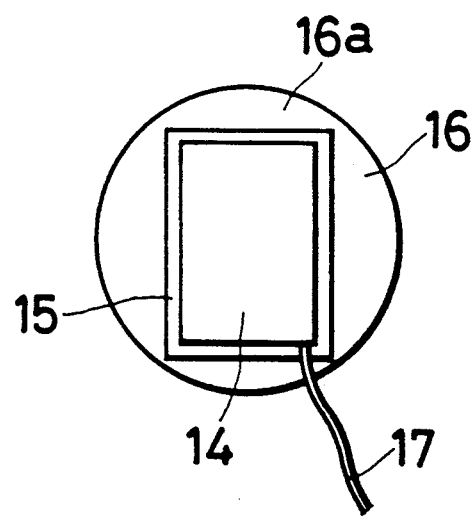
FIG. 6 is a front view of the embodiment shown in FIG. 5.

FIG. 5 is a cross-sectional view of a part of another embodiment of the invention and FIG. 6 is a front view thereof. A displacement detecting element 14 is attached to a part of an adhesive tape 16 via an elastic body 15. The elastic body 15 is, however, not necessary. Mastication can be measured by attaching a part 16a of the adhesive tape 16 at the portion not covering the displacement detecting element 14, and the elastic body 15 to a part of the side of the face 2 of a subject 1. A flexible lead wire 17 is connected to the displacement detecting element 14. The remaining elements are the same as those in the embodiment previously described.

When a ceramic piezoelectric element is used as the displacement detecting element 3 so as to have a rigid structure, the elastic body 11 is substituted with a rigid member in order to enable the detection of piezoelectricity in the thickness direction of the ceramic piezoelectric element.

In accordance with the invention, mastication can be measured by observing the waveform displayed on the oscilloscope or the like generated by the displacement detecting element attached to part of the side of the face operatively connected to the oscilloscope or the like.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing descriptions. And, all changes which come within the meaning and the range of equivalency of the claims are therefore intended to be embraced therein.

What is claimed is:

1. An apparatus for detecting mastication, the apparatus comprising:
   detecting means for detecting a displacement of a part of the side of a face, said detecting means comprising a flexible plate-like detecting element of a high-molecular weight polymer of piezoelectric material; and
   holding means for securing said plate-like detecting element in a position in close contact with the part of the side of a face, said holding means including a housing, a body of resilient material disposed in said housing and over which body said detecting element is disposed, and a cover covering said detecting element and secured to said housing.

2. An apparatus as claimed in claim 1, wherein said detecting element of piezoelectric material has a bimorph structure.

3. An apparatus as claimed in claim 2, wherein a respective said plate-like detecting element, a respective said body of resilient material, and a respective cover are provided for each side of the face,
   said holding means further includes a band-like U-shaped elastic member for positioning each said plate-like detecting element over part of a respective side of the face,
   each respective said plate-like detecting element is convex in a direction towards the respective cover which covers the detecting element, and
   each respective said body of resilient material is thicker at the center thereof than at the periphery thereof.

4. An apparatus as claimed in claim 1, wherein a respective said plate-like detecting element, a respective said body of resilient material, and a respective cover are provided for each side of the face,
   said holding means further includes a band-like U-shaped elastic member for positioning each said plate-like detecting element over part of a respective side of the face,
   each respective said plate-like detecting element is convex in a direction towards the respective cover which covers the detecting element, and
   each respective said body of resilient material is thicker at the center thereof than at the periphery thereof.

5. An apparatus for detecting mastication, the apparatus comprising:
   detecting means for detecting a displacement of a part of the side of a face, said detecting means comprising a flexible plate-like detecting element of a high-molecular weight polymer of piezoelectric material; and
   holding means for securing said plate-like detecting element in a position in close contact with the part of the side of a face, said holding means including adhesive tape secured to said detecting element, said adhesive tape attachable to the side of a face to secure said element in said position.

6. An apparatus as claimed in claim 5, wherein said detecting element of piezoelectric material has a bimorph structure.

7. An apparatus as claimed in claim 6, wherein a respective said plate-like detecting element, and a respective piece of said adhesive tape are provided for each side of the face, said holding means further includes a respective body of resilient material interposed between each said plate-like detecting element and the respective piece of adhesive tape secured thereto, and each respective said plate-like detecting element is convex in a direction toward the respective piece of adhesive tape secured thereto.

8. An apparatus as claimed in claim 5, wherein a respective said plate-like detecting element, and a respective piece of said adhesive tape are provided for each side of the face, said holding means further includes a respective body of resilient material interposed between each said plate-like detecting element and the respective piece of adhesive tape secured thereto, and each respective said plate-like detecting element is convex in a direction toward the respective piece of adhesive tape secured thereto.

9. An apparatus for measuring mastication, said apparatus comprising:

detecting means for detecting a displacement of a part of the side of a face, said detecting means comprising a flexible plate-like detecting element of a high-molecular weight polymer of piezoelectric material;

holding means for securing said plate-like detecting element in a position in close contact with the part of the side of a face, said holding means including a housing, a body of resilient material disposed in said housing and over which body said detecting element is disposed, and a cover covering said detecting element and secured to said housing;

processing means operatively connected to said detecting means for receiving an output of said detecting means indicative of the displacement of a part of the side of a face, and for processing said output into a measurement of mastication; and display means operatively connected to said processing means for displaying the measurement of mastication in response to the processing carried out by said processing means.

10. An apparatus as claimed in claim 9, wherein said display means displays the measurement of mastication as a waveform.

11. An apparatus as claimed in claim 10, wherein said processing means includes pulse generating means for generating pulses corresponding to the output, counting means for counting the pulses, integrating means for integrating the pulses to measure mastication energy represented by the output, and noise detecting means for discriminating noise included in the pulses.

12. An apparatus as claimed in claim 9, wherein said processing means includes pulse generating means for generating pulses corresponding to the output, counting means for counting the pulses, integrating means for integrating the pulses to measure mastication energy represented by the output, and noise detecting means for discriminating noise included in the pulses.

13. An apparatus for measuring mastication, said apparatus comprising:

detecting means for detecting a displacement of a part of the side of a face, said detecting means comprising a flexible plate-like detecting element of a high-molecular weight polymer of piezoelectric material;

holding means for securing said plate-like detecting element in a position in close contact with the part of the side of a face, said holding means including adhesive tape secured to said detecting element, said adhesive tape attachable to the side of a face to secure said element in said position;

processing means operatively connected to said detecting means for receiving an output of said detecting means indicative of the displacement of a part of the side of a face, and for processing said output into a measurement of mastication; and display means operatively connected to said processing means for displaying the measurement of mastication in response to the processing carried out by said processing means.

14. An apparatus as claimed in claim 13, wherein said display means displays the measurement of mastication as a waveform.

15. An apparatus as claimed in claim 14, wherein said processing means includes pulse generating means for generating pulses corresponding to the output, counting means for counting the pulses, integrating means for integrating the pulses to measure mastication energy represented by the output, and noise detecting means for discriminating noise included in the pulses.

16. An apparatus as claimed in claim 13, wherein said processing means includes pulse generating means for generating pulses corresponding to the output, counting means for counting the pulses, integrating means for integrating the pulses to measure mastication energy represented by the output, and noise detecting means for discriminating noise included in the pulses.

17. A method for measuring mastication, said method comprising:

providing detecting means including a flexible plate-like element of piezoelectric material for detecting a displacement thereof, and a holding means to which said detecting means is secured, the holding means including a housing, a body of resilient material disposed in said housing and over which body said detecting element is disposed, and a cover covering said detecting element and secured to said housing;

providing processing means operatively connected to said detecting means for receiving an output of said detecting means indicative of the displacement of said detecting element, and for processing said output into a measurement of the displacement;

providing display means operatively connected to said processing means for displaying the measurement of mastication in response to the processing carried out by said processing means; and securing said detecting element over a part of the side of a face with said holding means so that displacements of said detecting element caused by movement of the part of the side of a face during mastication are detected by said detecting means, are output by said detecting means, are processed by said processing means into a measurement of mastication, and are displayed by said display means as the measurement of mastication.

18. An apparatus as claimed in claim 17, wherein the step of providing a display means comprises providing a display means that will display the measurement of mastication as a waveform.

19. A method for measuring mastication, said method comprising:
providing detecting means including a flexible plate-like element of piezoelectric material for detecting a displacement thereof, and a holding means to which said detecting means is secured, the holding means including adhesive tape secured to said detecting element;
providing processing means operatively connected to said detecting means for receiving an output of said detecting means indicative of the displacement of said detecting element, and for processing said output into a measurement of the displacement;
providing display means operatively connected to said processing means for displaying the measurement of mastication in response to the processing carried out by said processing means; and
securing said detecting element over a part of the side of a face with said adhesive tape so that displacements of said detecting element caused by movement of the part of the side of a face during mastication are detected by said detecting means, are output by said detecting means, are processed by said processing means into a measurement of mastication, and are displayed by said display means as the measurement of mastication.

20. An apparatus as claimed in claim 19, wherein the step of providing a display means comprises providing a display means that will display the measurement of mastication as a waveform.

21. An apparatus for detecting mastication, the apparatus comprising:
detecting means for detecting a displacement of a part of the side of a face, said detecting means comprising a flexible plate-like detecting element of a compound of ceramic piezoelectric material and a high-molecular weight polymer of piezoelectric material; and
holding means for securing said plate-like detecting element in a position in close contact with the part of the side of a face, said holding means including a housing, a body of resilient material disposed in said housing and over which body said detecting element is disposed, and a cover covering said detecting element and secured to said housing.

22. An apparatus for detecting mastication as claimed in claim 21, wherein said plate-like detecting element of a compound of piezoelectric materials has a bimorph structure.

23. An apparatus as claimed in claim 22, wherein a respective said plate-like detecting element, a respective said body of resilient material, and a respective cover are provided for each side of the face,
said holding means further includes a band-like U-shaped elastic member for positioning each said plate-like detecting element over part of a respective side of the face,
each respective said plate-like detecting element is convex in a direction towards the respective cover which covers the detecting element, and
each respective said body of resilient material is thicker at the center thereof than at the periphery thereof.

24. An apparatus as claimed in claim 21, wherein a respective said plate-like detecting element, a respective said body of resilient material, and a respective cover are provided for each side of the face,
said holding means further includes a band-like U-shaped elastic member for positioning each said plate-like detecting element over part of a respective side of the face,
each respective said plate-like detecting element is convex in a direction towards the respective cover which covers the detecting element, and
each respective said body of resilient material is thicker at the center thereof than at the periphery thereof.

25. An apparatus for detecting mastication, the apparatus comprising:
detecting means for detecting a displacement of a part of the side of a face, said detecting means comprising a flexible plate-like detecting element of a compound of ceramic piezoelectric material and a high-molecular weight polymer of piezoelectric material; and
holding means for securing said plate-like detecting element in a position in close contact with the part of the side of a face, said holding means including adhesive tape secured to said detecting element, said adhesive tape attachable to the side of a face to secure said element in said position.

26. An apparatus for detecting mastication as claimed in claim 25, wherein said plate-like detecting element of a compound of piezoelectric materials has a bimorph structure.

27. An apparatus as claimed in claim 26, wherein a respective said plate-like detecting element, and a respective piece of said adhesive tape are provided for each side of the face,
said holding means further includes a respective body of resilient material interposed between each said plate-like detecting element and the respective piece of adhesive tape secured thereto, and
each respective said plate-like detecting element is convex in a direction toward the respective piece of adhesive tape secured thereto.

28. An apparatus as claimed in claim 25, wherein a respective said plate-like detecting element, and a respective piece of said adhesive tape are provided for each side of the face,
said holding means further includes a respective body of resilient material interposed between each said plate-like detecting element and the respective piece of adhesive tape secured thereto, and
each respective said plate-like detecting element is convex in a direction toward the respective piece of adhesive tape secured thereto.

29. An apparatus for measuring mastication, said apparatus comprising:
detecting means for detecting a displacement of a part of the side of a face, said detecting means comprising a flexible plate-like detecting element of a compound of ceramic piezoelectric material and a high-molecular weight polymer of piezoelectric material;
holding means for securing said plate-like detecting element in a position in close contact with the part of the side of a face, said holding means including a housing, a body of resilient material disposed in said housing and over which body said detecting element is disposed, and a cover covering said detecting element and secured to said housing;
processing means operatively connected to said detecting means for receiving an output of said detecting means indicative of the displacement of a part of the side of a face, and for processing said output into a measurement of mastication; and display means operatively connected to said processing means for displaying the measurement of mastication in response to the processing carried out by said processing means.

30. An apparatus as claimed in claim 29, wherein said display means displays the measurement of mastication as a waveform.

31. An apparatus as claimed in claim 30, wherein said processing means includes pulse generating means for generating pulses corresponding to the output, counting means for counting the pulses, integrating means for integrating the pulses to measure mastication energy represented by the output, and noise detecting means for discriminating noise included in the pulses.

32. An apparatus as claimed in claim 29, wherein said processing means includes pulse generating means for generating pulses corresponding to the output, counting means for counting the pulses, integrating means for integrating the pulses to measure mastication energy represented by the output, and noise detecting means for discriminating noise included in the pulses.

33. An apparatus for measuring mastication, said apparatus comprising:

detecting means for detecting a displacement of a part of the side of a face, said detecting means comprising a flexible plate-like detecting element of a compound of ceramic piezoelectric material and a high-molecular weight polymer of piezoelectric material;

holding means for securing said plate-like detecting element in a position in close contact with the part of the side of a face, said holding means including adhesive tape secured to said detecting element, said adhesive tape attachable to the side of a face to secure said element in said position;

processing means operatively connected to said detecting means for receiving an output of said detecting means indicative of the displacement of a part of the side of a face, and for processing said output into a measurement of mastication; and display means operatively connected to said processing means for displaying the measurement of mastication in response to the processing carried out by said processing means.

34. An apparatus as claimed in claim 33, wherein said display means displays the measurement of mastication as a waveform.

35. An apparatus as claimed in claim 34, wherein said processing means includes pulse generating means for generating pulses corresponding to the output, counting means for counting the pulses, integrating means for integrating the pulses to measure mastication energy represented by the output, and noise detecting means for discriminating noise included in the pulses.

36. An apparatus as claimed in claim 33, wherein said processing means includes pulse generating means for generating pulses corresponding to the output, counting means for counting the pulses, integrating means for integrating the pulses to measure mastication energy represented by the output, and noise detecting means for discriminating noise included in the pulses.

* * * * *